United States Patent [19]

Friedheim

[11] Patent Number: 4,514,390
[45] Date of Patent: Apr. 30, 1985

[54] MELAMINYLTHIOARSENITES

[75] Inventor: Ernst A. H. Friedheim, New York, N.Y.

[73] Assignee: The Rockefeller University, New York, N.Y.

[21] Appl. No.: 367,562

[22] Filed: Apr. 12, 1982

[51] Int. Cl.³ .................. C07D 251/70; C07F 9/80; C07F 9/65; A61K 31/53
[52] U.S. Cl. .................................. 514/184; 544/181
[58] Field of Search .............. 544/197, 181; 424/249

[56] References Cited

U.S. PATENT DOCUMENTS

| | | | |
|---|---|---|---|
| 2,295,574 | 9/1942 | Friedheim | 544/181 |
| 2,390,091 | 12/1945 | Friedheim | 544/181 |
| 2,400,547 | 5/1946 | Friedheim | 544/181 |
| 2,422,724 | 6/1947 | Friedheim | 544/181 |
| 2,593,434 | 4/1952 | Friedheim | 544/181 |
| 2,659,723 | 11/1953 | Friedheim | 544/181 |
| 3,974,148 | 8/1976 | Friedheim | 544/181 |

Primary Examiner—John M. Ford
Attorney, Agent, or Firm—Wyatt, Gerber, Shoup, Scobey and Badie

[57] ABSTRACT

Compounds of the formula

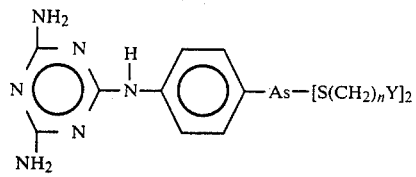

wherein Y is selected from the group consisting of $NH_2$,

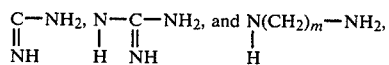

and n and m are both integers from 2 to 12 with the proviso that the value of n plus m is no more than 12, and the pharmaceutically acceptable acid addition salts thereof, are useful in the treatment of trypanocide and macrofilaricide infections.

18 Claims, No Drawings

MELAMINYLTHIOARSENITES

This invention was made with government support under contract number DAMD17-79-C-9148 awarded by the Department of Defense. The United States Government has certain rights in this invention.

BACKGROUND OF THE INVENTION

The compound represented by the formula

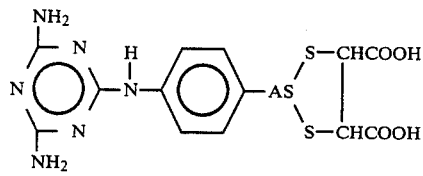

I and certain of its derivatives such as the disodium salt are well known as trypanocidal and macrofilaricidal agents.

The usefulness of the compounds is impaired by the limited stability of their solutions in water. As a result, it is necessary to package the products in the form of a dry powder which must be taken up in water just prior to use. This is a distinct disadvantage under field conditions in developing countries which are the principal sites of such infections. One such infection is commonly known as African Sleeping Sickness. It results from infections by *T. gambiense* and *T. rhodesiense*. Another is onchocerciasis, a non-fatal but disfiguring and blinding disease caused by the filarial worm *Onchocera volvulus*.

There is a definite need for anti-infective agents useful for the treatment of such infections, but not suffering the disadvantage of instability. More specifically, there is a need for trypanocidal and macrofilaricidal agents which will remain stable in a liquid medium, preferably aqueous media.

THE INVENTION

It has now been discovered that novel melaminylthioarsenites which are trypanocidal and macrofilaricidal agents can be prepared. They are therefore useful for treating infections caused by trypanosomes or filaria. They can be provided as the principal active agent in therapeutically useful compositions in association with pharmaceutically acceptable excipients. The compounds of this invention may be represented by the formula:

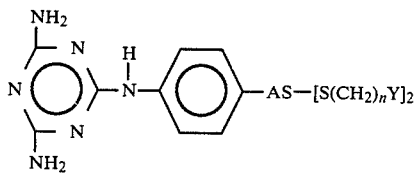

II wherein Y is selected from the group consisting of $NH_2$,

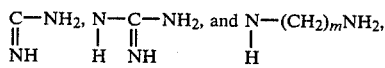

and n and m are both integers from 2 to 12 with the proviso that the value of n plus m is no more than 12.

The invention also includes pharmaceutically acceptable acid solution salts of the free bases within its scope.

The compounds of the invention are obtained by reaction of melarsenoxide with an appropriate thiol. The reaction can be represented by the equation:

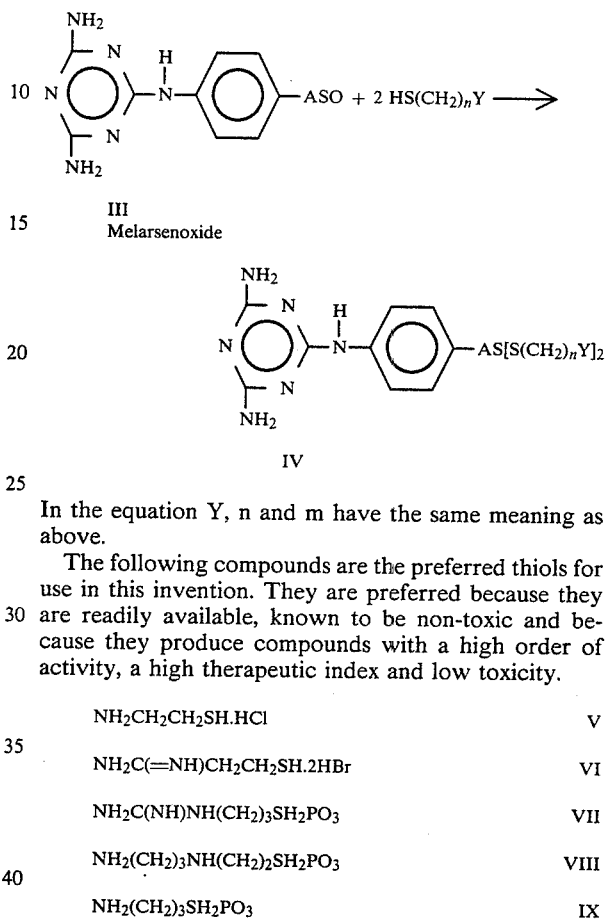

In the equation Y, n and m have the same meaning as above.

The following compounds are the preferred thiols for use in this invention. They are preferred because they are readily available, known to be non-toxic and because they produce compounds with a high order of activity, a high therapeutic index and low toxicity.

| | |
|---|---|
| $NH_2CH_2CH_2SH.HCl$ | V |
| $NH_2C(=NH)CH_2CH_2SH.2HBr$ | VI |
| $NH_2C(NH)NH(CH_2)_3SH_2PO_3$ | VII |
| $NH_2(CH_2)_3NH(CH_2)_2SH_2PO_3$ | VIII |
| $NH_2(CH_2)_3SH_2PO_3$ | IX |

It will be noted that the first two compounds are acid addition salts. The last three compounds are esters. In the course of the reaction, the esters rearrange so that the final products are acid addition salts.

Pharmaceutically acceptable acid addition salts are those containing non-toxic anions and include, for example, hydrochloric, hydrobromic, sulfuric, phosphoric, acetic, lactic, citric, tartaric, succinic, maleic, gluconic and saccharic acids. These acid addition salts are prepared by standard reactions either directly from the initial reaction or from the free base by reaction with the selected acid.

The general procedure for the preparation of the compounds of this invention is to react melarsenoxide with the selected thiol in an aqueous or lower alkanol medium at a temperature of from 40° to 100° C. until all of the reactants have dissolved. The reaction products separate as a viscous bottom layer. The reaction solvent, which may be a mixture of water and a lower alkanol, preferably methanol or ethanol is separated, suitably by decantation. The product may be purified by repeated recrystallization together with trituration with a dehydrating solvent, preferably ethanol. The preferred recrystallization solvent is water which may contain a small amount of ethanol, e.g. up to 20% by weight.

It is preferred to utilize a molar excess of thiol, i.e. more than two moles of thiol per mole of melarsenoxide. This insures as complete a reaction as possible of the toxic melarsenoxide and limits the amount which may be present as a contaminant in the final product. It is preferred to use at least a 10% molar excess of thiol, and for most purposes an excess of from 10 to 20% is acceptable.

The thiols may be reacted either as free thiols, phosphothionites, or as acid salts such as the hydrochloride or hydrobromide. Accordingly, a product of the invention may be obtained as a free base or an acid addition salt.

The preferred products of the invention are those represented by the formulas:

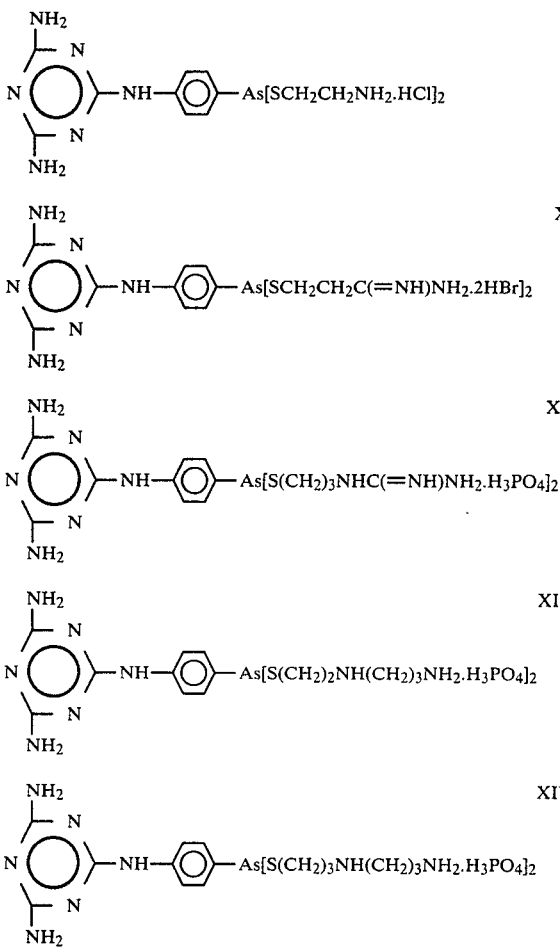

From these salts the free cationic melaminylthioarsenites can be prepared according to conventional methods. The cationic thioarsenites of the present invention are white powders, soluble in water, dilute acids and alkali, insoluble in acetone, chloroform, and ether. They have no sharp melting point and decompose above 200° C. They are useful for the treatment of parasitic diseases such as trypanosomiasis and filariasis, and onchocerciasis.

The products of this invention may be administered alone but will generally be administered with pharmaceutically acceptable, non-toxic carriers, the proportions of which are determined by the suitability and chemical nature of the particular carrier, the chosen route of administration, and standard pharmaceutical practice. For example, in combatting various infections or in maintaining therapeutically effective levels in the blood or tissue they may be administered orally in the form of tablets or capsules containing such excipients as starch, milk sugar, certain types of clay, etc. They may be enteric coated so as to be more resistant to the acid and digestive enzymes of the stomach. For intravenous and intramuscular administration they may be used in the form of a sterile solution containing other solutes, for example, enough saline or glucose to make the solution isotonic.

The compounds of the invention are orders of magnitude more stable than related prior art compounds which have been similarly employed. For example, if the disodium salt of Compound I the first formula shown above is dissolved in 1% water solution and held at 37° C., the solution becomes slightly cloudy after only 12 hours. A precipitate forms in 5 days. In contrast, Compounds X and XIII of this invention in 1% aqueous solution have been held at 37° C. for 5 days while still remaining clear. In fact, the solutions remain clear for as long as 3 months at 100° C.

The compounds of this invention have been screened for useful activity.

The test for trypanocidal activity is as described by Rane et al., Amer. J. Trop. Med. Hug. 25:394(1976).

This test system is patterned after the one developed and employed in testing of compounds for activity against *Plasmodium berghei* malaria in mice. The trypanosomiasis system is based on comparisons of responses to test compounds by ICR/HA Swiss mice infected with the Wellcome CT strain of *T. rhodesiense* as expressed in mean survival times compared with mean survival times of untreated controls.

Using a standard inoculum, it is possible to produce a uniform disease fatal to 100% of untreated animals within 4 to 6 days with a mean survival time of 4.45±0.25 days.

Test mice, six weeks of age, weighing 30–32 grams receive an intraperitoneal injection of 0.5 ml of a 1:50,000 dilution of heparinized heart blood drawn from donor mice infected 3 days earlier. Compounds are given as a single dose in peanut oil about two hours after parasite inoculation. Five mice per drug level, 20 infected untreated (negative) controls, and 10 infected positive controls are routinely used per test. Positive controls are mice infected and treated at 40 mg/kg with Stilbamidine Isethionate. Routinely compounds are first tested by the subcutaneous route of administration. If a compound is found to be active, it is retested for confirmation at selected drug levels and if the activity is confirmed it is tested by the oral route of administration.

Deaths prior to the fourth day, when untreated controls begin to die, are regarded as non-parasitic and are scored as "toxic deaths." Treated animals are kept under observation for 30 days. Survivors at the end of this period of time are considered as "cured." An increase of 100% in mean survival time is considered the minimum effective ("active") response for a candidate compound. In calculating mean survival times, toxic deaths and 30-day survivors are not included.

Using this test it was found that with Compound XII the $LD_{50}$ was of the order of 400 mg/kg of body weight and the $DCur_{50}$ (dose curative—50%) was of the order of 0.16 mg/kg of body weight. This corresponds to a therapeutic index of more than 2,000.

The filaricidal activity of Compound XIII was tested in gerbils infected with *L. carinii* according to the standard method employed at the WHO screening center at the Justes Liebig University in Giessen, West Germany. The results, as a function of dose, are shown in the following table.

TABLE I

Filaricidal Activity of Compound XIII

| Dose Mg/Kg × 5 SC[1] | % Reduction Microfilaria | Adult Worms[2] |
|---|---|---|
| 1.56 | 18.1 | 0 |
| 3.12 | 89.2 | 100 |
| 6.25 | 94.7 | 100 |
| 12.5 | 71.7 | 100 |
| 25.0 | 97.2 | 100 |

[1]Subcutaneous treatment for 5 days, sacrificed on the forty second day after treatment.
[2]Percent reduction of living worms compared to untreated controls.

The following non-limiting examples are given by way of illustration only. All temperatures are in degrees Centigrade.

EXAMPLE 1—COMPOUND X

A solution of 3.6 g III in 72 ml boiling EtOH is stirred into a solution of 3.0 g of V in 30 ml boiling EtOH. A white precipitate is formed which, after cooling to 10°, is filtered off, washed with EtOH and dried in vacuo over $P_2O_5$. X is reprecipitated by cooling out of boiling water. Yield 5.0 g. White powder, soluble in water, insoluble in MeOH, EtOH, chloroform, ether, unchanged dissolved in boiling water for 1 month.

EXAMPLE 2—COMPOUND XI 10 g III are dissolved in a solution of 20.2 g VI in 200 ml boiling water. On cooling to 0° of the filtered reaction, mixture XI precipitates, is purified by 3 reprecipitations by cooling of the hot aqueous solution, filtered off, washed with acetone and dried in vacuo. Yield: 7.1 g. XII is a white hygroscopic powder, soluble in water, EtOH and MeOH, insoluble in acetone, ethylacetate, ether, chloroform. A 1% solution of XI in water remains unchanged for 4 weeks.

EXAMPLE 3—COMPOUND XII

XII 5 g III are dissolved, with stirring, in a solution of 5.6 g VII in 100 ml boiling MeOH. After cooling to 0°, the reaction mixture is filtered and added to 200 ml ether. The reaction product precipitates as a viscous colorless syrup, which is separated by decantation, washed with 3 portions of 50 ml ether and dried in vacuo. The resulting crusts are soluble in water. EtOH and MeOH, insoluble in ether, chloroform and ethylacetate.

EXAMPLE 4—COMPOUND XIII 12 g VII are dissolved in 100 ml of water. 8 g III are added with stirring, while the mixture is brought to a boil. The resulting solution is filtered hot. On standing at 2° a colorless viscous bottom layer is formed. The supernatant is decanted. The bottom layer is dissolved in 50 ml boiling water and precipitated again by cooling. This procedure is repeated twice. After the last decantation the bottom layer has turned into a white powder, which is filtered off and dried in vacuo over $P_2O_5$. Yield 14.3 g. XIII is a white powder, sparingly soluble in cold water, soluble in hot water, dilute mineral acids, glacial acetic acid, and insoluble in EtOH, MeOH, acetone, chloroform and ether. A 1% solution of XIII in water remains unchanged at 100° C. for 1 month.

EXAMPLE 5—COMPOUND XIV 10 g III are dissolved with stirring in a solution of 10.1 g IX in 100 ml boiling water. The filtered solution, on standing at 0°, deposits a clear viscous bottom layer which is separated from the supernatant by decantation. On trituration with 100 ml EtOH, the bottom layer becomes solid, granular. It is filtered off and dried in vacuo. The yield is 18 g. The reaction product is purified by dissolving in the minimal amount of boiling water, followed by cooling and treatment with EtOH as above. XIV is a white powder, soluble in water, insoluble in EtOH, MeOH, acetone, chloroform and ether. A 1% solution of XIV in water remains unchanged at 100° for 4 weeks.

What is claimed is:

1. A compound represented by the formula $$\text{(triazine ring with two } NH_2 \text{ groups)} - NH - \text{(phenyl)} - As - [S(CH_2)_nY]_2$$

wherein Y is selected from the group consisting of $NH_2$, $$\underset{NH}{\overset{\|}{C}}-NH_2, \quad \underset{H}{\overset{}{N}}-\underset{NH}{\overset{\|}{C}}-NH_2 \text{ and } \underset{H}{\overset{}{N}}(CH_2)_m-NH_2,$$

and n and m are both integers from 2 to 12 with the proviso that the value of n plus m is no more than 12, and the pharmaceutically acceptable acid addition salts thereof.

2. A compound as in claim 1 of the formula $$\text{(diamino-triazine)} - NH - \text{(phenyl)} - As[SCH_2CH_2NH_2 \cdot HCl]_2.$$

3. A compound as in claim 1 of the formula $$\text{(diamino-triazine)} - NH - \text{(phenyl)} - As[SCH_2CH_2C(=NH)NH_2 \cdot 2HBr]_2.$$

4. A compound as in claim 1 of the formula $$\underset{NH_2}{\overset{NH_2}{\underset{|}{\overset{|}{N}}}}\text{(ring)}-NH-\text{(ring)}-As[S(CH_2)_3NHC(=NH)NH_2 \cdot H_3PO_4]_2.$$

5. A compound as in claim 1 of the formula $$\underset{NH_2}{\overset{NH_2}{\underset{|}{\overset{|}{N}}}}\text{(ring)}-NH-\text{(ring)}-As[S(CH_2)_2NH(CH_2)_3NH_2 \cdot H_3PO_4]_2.$$

6. A compound as in claim 1 of the formula $$\underset{NH_2}{\overset{NH_2}{\underset{|}{\overset{|}{N}}}}\text{(ring)}-NH-\text{(ring)}-As[S(CH_2)_3NH(CH_2)_3NH_2 \cdot H_3PO_4]_2.$$

7. A composition useful for treating infections caused by trypanosomes or filaria comprising a pharmaceutically acceptable carrier and, as the principal active ingredient in an amount which is effective for treating such infections, a compound of the formula:

$$\underset{NH_2}{\overset{NH_2}{\underset{|}{\overset{|}{N}}}}\text{(ring)}-\overset{H}{\underset{|}{N}}-As-[S(CH_2)_nY]_2$$

wherein Y is selected from the group consisting of $NH_2$, $$\underset{NH}{\overset{\|}{C}}-NH_2, \ \ N-\underset{NH}{\overset{\|}{C}}-NH_2 \ \ \text{and} \ \ N(CH_2)_m-NH_2,$$
$$\phantom{xx}\ \ \ \ \ \ \ \ \ \ \ \ \ \ \ \ \ \ |\ \ \ \ \ \ \ \ \ \ \ \ \ \ \ \ \ \ \ \ \ \ |$$
$$\phantom{xx}\ \ \ \ \ \ \ \ \ \ \ \ \ \ \ \ \ \ H\ \ \ \ \ \ \ \ \ \ \ \ \ \ \ \ \ H$$

and n and m are both integers from 2 to 12 with the proviso that the value of n plus m is no more than 12, and the pharmaceutically acceptable acid addition salts thereof.

8. A composition of claim 7 comprising a pharmaceutically acceptable carrier and, as the principal active ingredient, a compound of the formula:

$$\underset{NH_2}{\overset{NH_2}{\underset{|}{\overset{|}{N}}}}\text{(ring)}-NH-\text{(ring)}-As[SCH_2CH_2NH_2 \cdot HCl]_2.$$

9. A composition of claim 7 comprising a pharmaceutically acceptable carrier and, as the principal active ingredient, a compound of the formula:

$$\underset{NH_2}{\overset{NH_2}{\underset{|}{\overset{|}{N}}}}\text{(ring)}-NH-\text{(ring)}-As[SCH_2CH_2C(=NH)NH_2 \cdot 2HBr]_2.$$

10. A composition of claim 7 comprising a pharmaceutically acceptable carrier and, as the principal active ingredient, a compound of the formula:

$$\underset{NH_2}{\overset{NH_2}{\underset{|}{\overset{|}{N}}}}\text{(ring)}-NH-\text{(ring)}-As[S(CH_2)_3NHC(=NH)NH_2 \cdot H_3PO_4]_2.$$

11. A composition of claim 7 comprising a pharmaceutically acceptable carrier and, as the principal active ingredient, a compound of the formula:

$$\underset{NH_2}{\overset{NH_2}{\underset{|}{\overset{|}{N}}}}\text{(ring)}-NH-\text{(ring)}-As[S(CH_2)_2NH(CH_2)_3NH_2 \cdot H_3PO_4]_2.$$

12. A composition of claim 7 comprising a pharmaceutically acceptable carrier and, as the principal active ingredient, a compound of the formula:

$$\underset{NH_2}{\overset{NH_2}{\underset{|}{\overset{|}{N}}}}\text{(ring)}-NH-\text{(ring)}-As[S(CH_2)_3NH(CH_2)_3NH_2 \cdot H_3PO_4]_2.$$

13. A method of treating infections caused by trypanosomes or filaria of mammals which comprises treating a mammal in need of such treatment with a trypanocidally or macrofilaricidally effective amount of a compound represented by the formula:

$$\underset{NH_2}{\overset{NH_2}{\underset{|}{\overset{|}{N}}}}\text{(ring)}-\overset{H}{\underset{|}{N}}-\text{(ring)}-As-[S(CH_2)_nY]_2$$

wherein Y is selected from the group consisting of $NH_2$, $$\underset{NH}{\overset{||}{C}}-NH_2, \quad \underset{H}{\overset{N-}{\underset{|}{}}}\underset{NH}{\overset{||}{C}}-NH_2 \text{ and } \underset{H}{\overset{|}{N}}(CH_2)_m-NH_2,$$

and n and m are both integers from 2 to 12 with the proviso that the value of n plus m is no more than 12, and the pharmaceutically acceptable acid addition salts thereof.

14. A method of treating infections caused by trypanosomes or filaria as in claim 13 of mammals which comprises treating a mammal in need of such treatment with a trypanocidally or macrofilaricidally effective amount of a compound represented by the formula:

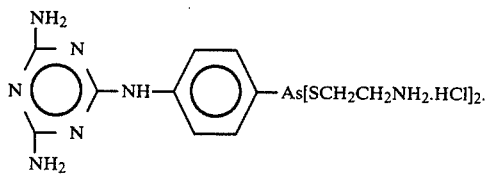

15. A method of treating infections caused by trypanosomes or filaria as in claim 13 of mammals which comprises treating a mammal in need of such treatment with a trypanocidally or macrofilaricidally effective amount of a compound represented by the formula:

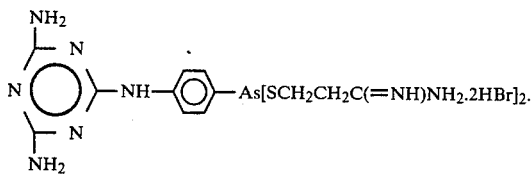

16. A method of treating infections caused by trypanosomes or filaria as in claim 13 of mammals which comprises treating a mammal in need of such treatment with a trypanocidally or macrofilaricidally effective amount of a compound represented by the formula:

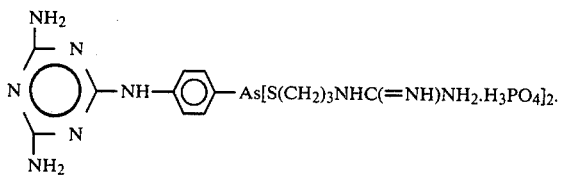

17. A method of treating infections caused by trypanosomes or filaria as in claim 13 of mammals which comprises treating a mammal in need of such treatment with a trypanocidally or macrofilaricidally effective amount of a compound represented by the formula:

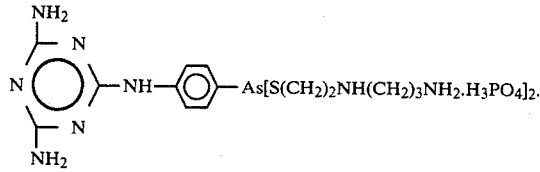

18. A method of treating infections caused by trypanosomes or filaria as in claim 13 of mammals which comprises treating a mammal in need of such treatment with a trypanocidally or macrofilaricidally effective amount of a compound represented by the formula:

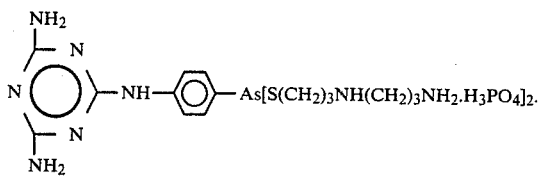

* * * * *

UNITED STATES PATENT AND TRADEMARK OFFICE

CERTIFICATE EXTENDING PATENT TERM
UNDER 35 U.S.C. § 156

PATENT NO. : 4,514,390

ISSUED : April 30, 1985

INVENTOR(S) : Ernst A. H. Friedheim

PATENT OWNER : The Rockefeller University

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,632 days from the original expiration date of the patent, April 30, 2002, with all rights pertaining thereto as provided by 35 U.S.C. § 156(b).

I have caused the seal of the Patent and Trademark Office to be affixed this 21st day of April 1997.

Bruce A. Lehman
Assistant Secretary of Commerce and
   Commissioner of Patents and Trademarks